United States Patent [19]

Scholl et al.

[11] Patent Number: 4,618,706

[45] Date of Patent: Oct. 21, 1986

[54] PROCESS FOR THE PREPARATION OF AROMATIC POLYISOCYANATES CONTAINING UREA AND/OR BIURET GROUPS

[75] Inventors: Hans-Joachim Scholl; Hans Hettel, both of Cologne, Fed. Rep. of Germany

[73] Assignee: Bayer Aktiengesellschaft, Leverkusen, Fed. Rep. of Germany

[21] Appl. No.: 364,945

[22] Filed: Apr. 2, 1982

[30] Foreign Application Priority Data

Apr. 10, 1981 [DE] Fed. Rep. of Germany ....... 3114638

[51] Int. Cl.$^4$ ............................................ C07C 127/24
[52] U.S. Cl. ..................................... 560/335; 521/159
[58] Field of Search ................... 260/453 AB; 560/335

[56] References Cited

U.S. PATENT DOCUMENTS

| | | | |
|---|---|---|---|
| 3,824,266 | 7/1974 | Dieterich et al. | 260/453 AB |
| 4,264,519 | 4/1981 | Hennig et al. | 260/453 AB |
| 4,292,255 | 9/1981 | Hennig et al. | 260/453 AR |

FOREIGN PATENT DOCUMENTS 1360019 8/1967 United Kingdom .
1078390 8/1967 United Kingdom .

OTHER PUBLICATIONS

Polyurethanes, Chemistry & Technology Part I p. 190 et seq., Saunders & Frisch, Interscience Publishers 1962.

*Primary Examiner*—Dolph H. Torrence
*Attorney, Agent, or Firm*—Gene Harsh; Joseph C. Gil; Thomas W. Roy

[57] ABSTRACT

This invention relates to a process for the preparation of aromatic polyisocyanates containing urea and/or biuret groups, optionally in the form of a mixture of homologues and/or isomers, by the reaction of aromatic diisocyanates with diamines having primary or secondary amino groups at about 20° to 180° C., and at an equivalent ratio of isocyanate groups to amino groups in the range of 5:1 to 100:1, at least 25 mol percent of the diisocyanates put into the process and/or at least 25 mol percent of the diamines put into the process being alkylphenylene diisocyanates or, respectively, alkyl-phenylene diamines, in which the alkyl substituents have 6 to 18 carbon atoms, and the use of the products of the process, optionally as solutions in excess starting diisocyanate, as isocyanate components in the production of polyurethanes.

4 Claims, No Drawings

PROCESS FOR THE PREPARATION OF AROMATIC POLYISOCYANATES CONTAINING UREA AND/OR BIURET GROUPS

BACKGROUND OF THE INVENTION

1. Field of the Invention

This invention relates to a new process for the preparation of new aromatic polyisocyanates containing urea and/or biuret groups by the reaction of diisocyanates with subequivalent quantities of primary and/or secondary diamines, in which the diisocyanates and/or diamines used as reactants consist wholly or in part of special diisocyanates described in more detail below and/or special diamines described in more detail below, and to the use of the products of the process as isocyanate components in the production of polyurethanes.

2. Description of the Prior Art

Polyisocyanates containing urea and/or biuret bonds are known (see e.g., 'Polyurethanes', Chemistry and Technology, Part I, by Saunders and Frisch, Interscience Publishers, (1962), pages 190 et. seq.).

Such urea and/or biuret bonds are normally obtained by the action of water on polyisocyanates, which entails the loss of valuable isocyanates.

British Pat. No. 1,078,390 describes the formation of biurets directly from diamines and aromatic polyisocyanates by carrying out this reaction in solvents having a boiling point below the boiling point of the isocyanate, e.g., chloroform. The disadvantage of this process is that the reaction must be followed by removal of the solvent by distillation. Direct reaction of the diamines given in the examples with the isocyanates described is not possible without solvents since the difficultly soluble polyureas which are formed instantly prevent further reaction of the isocyanate.

German Offenlegungsschrift No. 1,963,190 also describes a process in which aromatic polyamines containing primary amino groups can be directly reacted with polyisocyanates to form soluble biurets without the aid of solvents if the polyamines with primary amino groups have an attenuated nucleophilic character. The reactivity of the amines with isocyanates must be attenuated to such an extent that a homogeneous mixture of amine and isocyanate can be prepared before the two components begin to react. This requires the employment of very elevated temperatures, with the attendant risk of undesirable side reactions and the precipitation of solid constituents.

It was therefore an object of the present invention to provide a new process for the preparation of stable, liquid aromatic polyisocyanates containing urea and/or biuret groups from diamines and diisocyanates which may be carried out in the liquid phase without the aid of auxiliary solvents but at the usual temperatures employed for preparations without any insoluble urea and/or biuret constituents being found to precipitate.

This problem could be solved by the process according to the invention described below.

SUMMARY OF THE INVENTION

The present invention relates to a process for the preparation of aromatic polyisocyanates containing urea and/or biuret groups, optionally in the form of a mixture of homologues and/or isomers, by reacting aromatic diisocyanates which are free from urea and biuret groups with diamines which are free from urea and biuret groups and contain primary or secondary amino groups at about 20° to 180° C., and at an equivalent ration of isocyanate groups to amino groups within the range of about 5:1 to 100:1, wherein at least about 25 mol percent of the diisocyanates put into the reaction correspond to the formula:

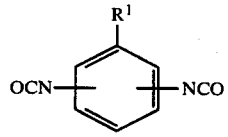

and/or at least about 25 mol percent of the diamines put into the reaction correspond to the formula:

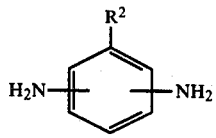

in which formulae, $R^1$ and $R^2$ may be identical or different and in each case denote saturated aliphatic hydrocarbons having 6 to 18 carbon atoms.

The invention also relates to the use of the aromatic polyisocyanates with urea and/or biuret groups obtained by the process according to the invention, optionally as solutions in excess starting diisocyanate, as isocyanate components in the production of polyurethanes by the isocyanate polyaddition process.

DETAILED DESCRIPTION OF THE INVENTION

Any aromatic diisocyanates may be used in the process according to the invention, for example those corresponding to the formula:

wherein Q denotes an aromatic hydrocarbon group having 6 to 15, preferably 6 to 13 carbon atoms, e.g., p-phenylene diisocyanate, 2,4- and 2,6-diisocyanato-toluene, 2,4'- and 4,4'-diisocyanatodiphenylmethane, 3,4'-diisocyanato-4-methyl-diphenylmethane, 3,2'-diisocyanato-4-methyl-diphenylmethane, 1,5-diisocyanatonaphthalene, 4,4'-diisocyanatodiphenylpropane(1,1) and any mixtures of such diisocyanates.

Any diamines with primary and/or secondary amino groups may be used in the process according to the invention, for example, those corresponding to the formula:

wherein

Q' denotes a group which corresponds to the definition of Q and may be identical or different from Q and $R^3$ denotes hydrogen or an alkyl group having 1 to 4 carbonatoms.

The following are examples of such diamines: p-phenylene diamine, 2,4 - and 2,6-diaminotoluene, N,N'-dimethyl-2,4-diaminotoluene, 2,4'- and/or 4,4'-diaminodiphenylmethane, 3,4'-diamino-4-methyl-diphenylmethane, 3,2'-diamino-4-methyl-diphenylmethane and 1,5-diamino-naphthalene. Any mixtures of such diamines may be used in the process according to the invention.

The only essential condition of the invention is that at least about 25 mol percent of the diisocyanates used in the process according to the invention correspond to the formula:

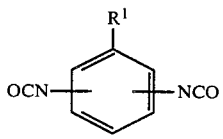

and/or at least about 25 mol percent of the diamines used in the process according to the invention correspond to the formula:

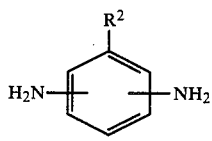

wherein $R^1$ and $R^2$ have the meaning already mentioned above.

A particularly preferred embodiment of the process according to the invention is that in which the diamines put into the process consist exclusively of diamines of the last-mentioned formula and the diisocyanates consist exclusively of diisocyanates with aromatically bound isocyanate groups of the type exemplified.

Particularly preferred for the process according to the invention are those diamines of the last-mentioned general formula according to the invention in which $R^2$ is a saturated aliphatic hydrocarbon group having from 8 to 15, preferably from 10 to 13 carbon atoms and which are in the form of mixtures of isomers and/or homologues.

The diamines of the last-mentioned general formula which are essential to this invention are obtained by dinitration of the underlying alkyl benzenes followed by conversion of the nitro groups into amino groups. The particularly preferred mixtures of homologues or isomers may be prepared, for example, by dinitrating alkyl benzenes in the form of commercial mixtures of homologues or isomers consisting preferably exclusively but at least to an extent of about 90% by weight of alkyl benzenes corresponding to the formula:

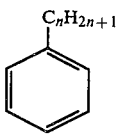

wherein n is an integer of from 8 to 15, preferably from 10 to 13, and which have a boiling range according to ASTM D 86 at 1013 mbar of about 10°-50° C., preferably about 20°-30° C. within the temperature range of about 270° C. to 330° C., and then converting the reaction product into the diamines.

The preparation of such alkyl benzene mixtures is carried out in known manner by the alkylation of benzene with commercial olefin mixtures or commercial alkyl chloride mixtures as described, for example, in Kirk Othmer, Encyclopedia of Chemical Technology, third edition, volume 2, (1978), on pages 50 to 61.

The alkyl benzenes are subsequently converted into the corresponding dinitro compounds by a known nitration reaction, for example in the temperature region of about 10°-30° C., using, for example, about 2-3 mol of concentrated nitric acid per mol of alkyl benzene, the nitric acid being used in the form of a mixture with concentrated sulphuric acid (nitrating acid). In the alkyl-substituted dinitrobenzenes obtained, more than about 95% of all the nitro groups are in the meta position to each other, according to nuclear resonance measurements. It may also be assumed that about 10 to 30% by weight of the dinitrated alkyl benzenes are 1-alkyl-2,6-dinitrobenzenes and about 70 to 90% by weight are 1-alkyl-2,4-dinitrobenzenes. This distribution of isomers, however, is by no means essential.

The next stage, for example, could be carried out equally well using dinitrated alkyl benzenes in which the above-mentioned isomers are present in different quantitative proportions. Thus, for example, the next stage could be carried out using 1-alkyl-2,4-dinitrobenzene in the 2,6-free form such as may be obtained, for example, by a 2-stage nitration of alkyl benzene by way of 1-alkyl-4-nitrobenzene isolated as intermediate stage.

The next stage consists of the known hydrogenation reaction of the nitro groups to the corresponding primary amino groups, for example, using Raney nickel as hydrogenation catalyst, e.g., at temperatures of about 20°-60° C. and under a hydrogen pressure of, for example, about 20 to 40 bar.

In the diamines of the above formula obtained from this hydrogenation, the position of the amino groups is, of course, in accordance with the remarks made above concerning the position of the nitro groups, and the nature of the group R is in accordance with the remarks made in the description of the alkyl benzenes used for their preparation.

As regards the nature of the diisocyanates corresponding to the formula:

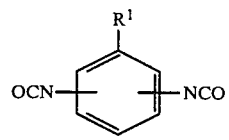

used instead of or together with the diamines which are essential to this invention, all the remarks made about the diamines apply correspondingly. Thee diisocyanates are obtained from the last-described diamines by the known phosgenation reaction which may be carried out, for example, by dissolving the diamine in an auxiliary solvent such as chlorobenzene and then introducing it drop-wise into a solution of phosgene in chlorobenzene with stirring and cooling at about −20° to 5° C., preferably about −10° to 0° C. (cold phosgenation), and thereafter heating the reaction mixture with continued stirring and introduction of phosgene to temperatures of about 80° to 130° C., preferably about 90° to 110° C. to convert the carbamic acid chloride initially formed into the required diisocyanate (hot phosgenation). The reaction mixture obtained is then worked up in known manner. Conversion of the diamines into the diisocyanates according to the invention may also be carried out by any other known method of phosgenation.

The process according to the invention may be carried out by introducing the diamine component into the polyisocyanate component with vigorous mixing at about 20° to 180° C., preferably about 30° to 150° C. The proportions of the reactants are chosen to provide an equivalent ratio of isocyanate groups to amino groups in the range of about 5:1 to 100:1, preferably about 5:1 to 40:1.

In preferred embodiments of the process according to the invention, the reaction is carried out in the presence of catalysts which accelerate the isocyanate addition reaction and/or in the presence of additives. For example, small quantities of alkylating agents may be used to prevent unwanted side reactions such as isocyanurate formation.

Examples of suitable catalysts include organic metal compounds such as zinc acetyl acetonate, cobalt acetyl acetonate, tin-(II)-octoate and dibutyl tin dilaurate. The above-mentioned acetyl acetonates are preferred. If used at all, these catalysts are used in quantities of about 0.001 to 2% by weight, preferably about 0.005 to 0.5% by weight, based on the reaction mixture.

Suitable alkylating agents are, for example, methyl iodide, dialkyl sulphates or aliphatic or aromatic sulphonic acid alkyl esters such as e.g., toluene sulphonic acid ethyl ester, which are used, if at all, in quantities of from about 0.001 to 2% by weight, preferably from about 0.01 to 1% by weight, based on the whole mixture.

Whether the process according to the invention gives rise primarily to polyisocyanates containing urea groups or to polyisocyanates containing biuret groups depends upon the reactivity of the reactants, the reaction temperature, the reaction time and the nature and quantity of any catalysts used.

It may be assumed that in a reaction carried out below about 100° C. without the aid of catalysts, polyisocyanates containing urea groups are primarily formed, whereas the product obtained above about 100° C. contains progressively increasing proportions of polyisocyanates containing biuret groups, whose formation can be accelerated catalytically. The process according to the invention may, of course, give rise to mixtures of polyisocyanates containing urea groups and polyisocyanates containing biuret groups. Since the starting diisocyanate is always used in excess in the process according to the invention, the products of the process are obtained in the form of solutions in excess unmodified starting diisocyanate from which they may be freed, for example, by thin layer distillation of the unreacted starting diisocyanate, although they are preferably used for the purpose of the invention in the form of the above-mentioned solutions.

The special advantage of the process according to the invention lies in the fact that due to the exclusive or partial use of the diisocyanates or diamines which are essential to the invention, no problems of crystallization occur. The process according to the invention thus invariably gives rise to solutions of the end products according to the invention in the starting diisocyanate without any solid content, regardless of whether or not the reaction is stopped at the stage of urea, for example, by cooling.

The process products according to the invention are suitable in particular in the form of the solutions obtained in the process according to the invention as isocyanate components for the production of polyurethanes by the isocyanate polyaddition process, i.e., by reaction with an isocyanate-reactive compound. It is immaterial for this purpose whether the products of the process consist mainly of polyisocyanates having urea groups or of polyisocyanates having biuret groups. The products according to the invention are suitable in particular for the production of polyurethane foams by the known methods of the art.

The following examples serve to illustrate the invention. All percentages given are percentages by weight.

Preparation of starting materials

Diamine mixture I (a) Nitration of an alkyl benzene mixture:

A mixture of 1136 ml of 98% nitric acid and 1584 ml of 96% sulphuric acid is introduced drop-wise with cooling into 1.97 kg of a mixture of linear alkyl benzene homologues in which the alkyl chains have a length of 10 to 13 C atoms with an average length of about 12 C atoms and which according to ASTM D 86 boils at 283° to 313° C. and 1013 mbar, the acid being added at such a rate that the reaction temperature is maintained at 10° to 15° C. When all the acid has been added, the mixture is stirred for 3 hours at 25°-30° C. The organic phase is then shaken on 10 kg of ice, washed neutral with sodium bicarbonate solution and again washed with water. The organic phase is separated and substantially freed from any residues of water by centrifuging. The liquid dinitroalkyl benzene mixture obtained is used for the next reaction stage without further purification.

Yield: 2.7 kg; $NO_2$ content: 27.5% (theoretical: 27.4%).

(b) Hydrogenation of the dinitroalkyl benzene mixture:

672 g of the dinitro compound of (a) are dissolved in 1700 ml of ethanol in a stirrer autoclave and 70 g of Raney nickel are added. The mixture is stirred at 40° C. and a hydrogen pressure of 20 to 40 bar until uptake of hydrogen is completed. The pressure is then released, the catalyst is removed by filtration and the ethanol is distilled off. 550 g of a crude amine mixture is obtained. It may be used either directly or after purification by distillation for the use according to the invention. The crude amine mixture has a nitrogen content of 10.06% (theoretical: 10.1%). 200 g of the crude amine mixture are distilled at reduced pressure. 167 g of diamine mixture is thus obtained as a fraction boiling at 185°-204° C./ 2,1 mbar (Yield: 83.5%).

| | Analysis (%): | | |
|---|---|---|---|
| | C | H | N |
| FOUND: | 78.6 | 11.5 | 10.0 |
| Theoretical: (based on $C_{18}H_{32}N_2$) | 78.3 | 11.6 | 10.1 |

Diisocyanate mixture I 3 liters of anhydrous chlorobenzene are introduced into a 6 liter 4-necked flask equipped with stirrer, thermometer, gas inlet tube and reflux condenser. About 800 g of phosgene are incorporated by condensation with stirring and cooling ($-10°$ C.). 550 g of the crude amine mixture described in the method of preparation of diamine mixture I, dissolved in 500 ml of chlorobenzene, are then introduced drop-wise with cooling at $-10°$ to $-5°$ C. As phosgene continues to be introduced, the solution subsequently heats up to about 30°

C. without further cooling. When the evolution of heat has died down, the reaction mixture is slowly heated to 100° C., and phosgene is introduced (a total of 970 g) until no further hydrogen chloride evolves. The excess phosgene is blown out with nitrogen and the solution is concentrated by evaporation under vacuum. 638 g of a crude isocyanate mixture having an isocyanate content of 25% (theoretical: 25.6%) are obtained. The diisocyanate thus obtained may be used for the process according to the invention without further purification or it may first be purified by distillation.

300 g of the diisocyanate mixture are distilled under reduced pressure. At a pressure of 2,2 mbar, 273 g of a virtually colorless mixture of diisocyanates corresponding to the following formula distill off at the temperature range of 185° to 203° C.;

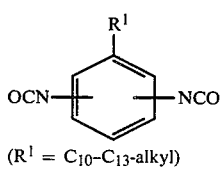

($R^1$ = $C_{10}$-$C_{13}$-alkyl)

This product shows no tendency to crystallization even when cooled to −50° C.

|  | Analysis (%): | | | |
| --- | --- | --- | --- | --- |
|  | NCO | C | H | N |
| FOUND: | 25.5 | 73.6 | 8.6 | 8.4 |
| Theoretical: (based on $C_{20}H_{28}N_2O_2$) | 25.6 | 73.2 | 8.5 | 8.5 |

According to nuclear resonance measurements, the isocyanate groups of the diisocyanate are arranged in the meta-position to each other. The main component of the mixture is 1-alkyl-2,4-diisocyanatobenzene.

EXAMPLE 1

1,000 g of a diisocyanate mixture consisting of 80% of 2,4- and 20% of 2,6-diisocyanatotoluene, 1 g of toluene sulphonic acid ethyl ester and 0.1 g of zinc acetyl acetonate are introduced into a 3-necked flask with stirrer, dropping funnel, internal thermometer and bubble counter under nitrogen and heated to 80° C. 83 g of diamine mixture I boiling at 185° to 204° C./2,1 mbar are then added dropwise with stirring at 80° C. during 1 hour. Stirring is then continued for 2 hours at 100° C. and 1.5 ml of benzoyl chloride are finally added as stabilizer. A polyisocyanate with an isocyanate content of 41.3% which has been extensively modified with biuret groups is obtained after cooling to room temperature. No precipitation of insoluble products occurred at any time during preparation of the modified polyisocyanate.

EXAMPLE 2

2,700 g of a diisocyanate mixture consisting of 80% of 2,4- and 20% of 2,6-diisocyanatotoluene, 2.7 g of toluene sulphonic acid ethyl ester and 0.3 g of zinc acetyl acetonate are heated to 80° C. as in Example 1 and reacted with 280 g of diamine mixture I. The reaction mixture is then stirred for 3 hours at 100° C. and stabilized with 2 g of benzoyl chloride. A polyisocyanate with an isocyanate content of 38.8% which has been substantially modified with biuret groups is obtained. No solid constituents were observed at any point.

EXAMPLE 3

1,000 g of a diisocyanate mixture consisting of 55% of 2,4'- and 45% of 4,4'-diisocyanatodiphenylmethane, 1 g of toluene sulphonic acid ethyl ester and 0.2 g of zinc acetyl acetonate are heated to 80° C., and 55 g of diamine mixture I are added within 1 hour. The reaction mixture is then stirred for 3 hours at 100° C. and stabilized with 1 g of benzoyl chloride. An extensively biuret-modified polyisocyanate having an isocyanate content of 29.0% is obtained, which is free from solid constituents.

Preparation of urea polyisocyanates

EXAMPLE 4

55 g of diamine mixture I are added in the course of 1 hour at 30° to 40° C. to 945 g of a diisocyanate mixture of 80% of 2,4- and 20% of 2,6-diisocyanatotoluene. The mixture is then stirred for 5 hours at 50° C. and stabilized with 1 g of benzoyl chloride. A liquid polyisocyanate having an isocyanate content of 44.2% and containing urea groups is obtained. The infrared spectrum shows that no by-products containing biuret are present (no absorption in the region of about 1,700 $cm^{-1}$).

Preparation of polyisocyanates containing urea groups and biuret groups

EXAMPLE 5

The reaction mixture was prepared as in Example 4 but stirring after preparation of the reaction mixture was carried out for 4 hours at 140° C. A liquid polyisocyanate containing urea and biuret groups and having an isocyanate content of 43.7% was obtained.

EXAMPLE 6

The reaction mixture of Example 4 was prepared by a preferred method according to the invention in that the reaction was carried out using 1 g of toluene sulphonic acid ethyl ester and 0.2 g of zinc acetyl acetonate and followed by 4 hours stirring at 100° C. The solution, stabilized with 1 g of benzoyl chloride, was found to have an isocyanate content of 43.0%. This proves that the urea groups to be produced according to Example 4 are to a large extent biuretized by the method of this Example.

EXAMPLE 7

860 g of diisocyanate mixture I, 1 g of toluene sulphonic acid ethyl ester and 0.2 g of zinc acetyl acetonate are heated to 80° C., and 140 g of diamine mixture I are added within 1 hour. The reaction mixture is then stirred for 4 hours at 110° C. and stabilized with 1 g of benzoyl chloride. A viscous, biuret-modified polyisocyanate with an isocyanate content of 15.1% is obtained. The product is free from solid constituents.

EXAMPLE 8

820 g of diisocyanate mixture I, 1 g of toluene sulphonic acid ethyl ester and 0.2 g of zinc acetyl acetonate are heated to 100° C. and reacted portionwise in the course of 1 hour with 12.2 g of 2,4-diaminotoluene, during which time the temperature is slowly raised to 140° C. Stirring is then continued for 4 hours at 140° C. and the reaction mixture is stabilized with 1 g of benzoyl chloride. A biuret-modified polyisocyanate having an isocyanate content of 20.1% is obtained in the form of a thin liquid.

EXAMPLE 9

870 g of diisocyanate mixture consisting of 80% of 2,4- and 20% of 2,6-diisocyanatotoluene, 1 g of toluene sulphonic acid ethyl ester and 0.1 g of zinc acetyl acetonate are heated to 120° C. A solution of 18 g of 2,4-diamino toluene in 14 g of diamine mixture I, heated to 100° C., is added dropwise in the course of 1 hour and the reaction mixture is then stirred for 3 hours at 140° C. and stabilized with 1 g of benzoyl chloride. The biuret-modified polyisocyanate is obtained as a thin liquid having an isocyanate content of 44.5%.

EXAMPLE 10

330 g of diisocyanate mixture I, 525 g of a diisocyanate mixture consisting of 80% of 2,4- and 20% of 2,6-diisocyanatotoluene, 1 g of toluene sulphonic acid ethyl ester and 0.2 g of zinc acetyl acetonate are heated to 130° C. 12 g of 2,4-diaminotoluene are introduced in the course of 1 hour and the reaction mixture is then stirred for 3 hours at 140° C. After stabilization with 1 g of benzoyl chloride, a biuret-modified polyisocyanate having an isocyanate content of 38.0% is obtained as a thin liquid.

EXAMPLE 11

Example 10 is repeated but in this case a solution of 18 g of 2,4-diaminotoluene in 14 g of diamine mixture I heated to 100° C. is added dropwise instead of 12 g of 2,4-diaminotoluene. After suitable working up, the product obtained is a thin liquid consisting of biuret-modified polyisocyanate having an isocyanate content of 36.2%.

EXAMPLE 12

1,000 g of a diisocyanate mixture consisting of 80% of 2,4- and 20% of 2,6-diisocyanatotoluene, 1 g of toluene sulphonic acid ethyl ester and 0.1 g of zinc acetyl acetonate are heated to 100° C. A solution of 10 g of 4,4'-diamino-diphenylmethane dissolved in 42 g of diamine mixture I is then added dropwise in the course of 1 hour. The reaction mixture is then stirred for 3 hours at 130° C. and stabilized with 0.5 g of benzoyl chloride. A biuret-modified polyisocyanate having an isocyanate content of 40.9% is obtained in the form of a thin liquid.

EXAMPLE 13

Preparation of a foam

When 46.1 parts by weight of the biuret-modified polyisocyanate of Example 1 (NCO: 41.3%) is vigorously mixed with a previously prepared mixture of 100 parts by weight of a trifunctional polyether polyol with OH number 28 which has been obtained by propoxylation of trimethylol propane followed by ethoxylation of the propoxylation product (total 13% by weight ethylene oxide), 3.0 parts by weight of water, 0.5 parts by weight of polysiloxane stabilizer, 2.0 parts by weight of diethanolamine and 0.6 parts by weight of a 33% solution of diethylene triamine in dipropylene glycol, the mixture foams up and solidifies to form a highly elastic flexible foam having the characteristics summarized in Table 1.

COMPARISON EXAMPLE 13a

Example 13 is repeated but instead of using the biuret polyisocyanate according to the invention, there are used 46.9 parts by weight of a commercial allophanate-modified polyisocyanate with an isocyanate content of 40,5% (Desmodur ® MT 58 of Bayer AG, Leverkusen, Germany).

This polyisocyanate is one conventionally used for the production of flexible polyurethane foams. The characteristics of the highly elastic flexible foams obtained are entered in the following Table 1.

TABLE 1

| Mechanical properties | Example 13 | Comparison Example 13a |
|---|---|---|
| Gross density (kg/m$^3$) | 35 | 35 |
| Tensile strength (kPa) | 100 | 75 |
| Elongation at break (%) | 150 | 100 |
| Compression resistance (kPa) at 40% deformation | 2.9 | 1.9 |
| Pressure deformation residue (%) at 90% deformation | 10 | 8 |

EXAMPLE 14

50.2 parts by weight of the biuret-modified polyisocyanate of Example 2 (NCO: 38.8%) are vigorously mixed with a previously prepared mixture of

| 100 parts by weight | of a trifunctional polyether polyol with OH number 35 obtained by the propoxylation of trimethylol propane followed by ethoxylation of the propoxylation product (total 13% ethylene oxide), |
|---|---|
| 3.0 parts by weight | of water |
| 0.5 parts by weight | of a polysiloxane stabilizer |
| 2.0 parts by weight | of diethanolamine |
| 0.2 parts by weight | of diethylene triamine |
| 0.1 parts by weight | of dimethylaminoethyl ether and |
| 0.1 parts by weight | of tin dioctoate, | and the resulting mixture is foamed up in an open mold. A highly elastic flexible foam having the following mechanical properties is obtained:

| Gross density (kg/m$^3$) | 37 |
|---|---|
| Tensile strength KPa | 90 |
| Elongation at break % | 125 |
| Compression resistance KPa at 40% deformation | 3.3 |
| Pressure deformation residue % (90% deformation) | 10 |

EXAMPLE 15

A polyisocyanate mixture consisting of 18.9 parts by weight of the biuret-modified polyisocyanate according to Example 2 and 25.1 parts by weight of an isomeric mixture of 80% 2,4- and 20% 2,6-diisocyanatotoluene (isocyanate content of the mixture: 44.2%) is intimately mixed with a previously prepared mixture of

| 100 parts by weight | of the trifunctional polyether polyol with OH number 35 of Example 14, |
|---|---|
| 3.0 parts by weight | of water |
| 0.5 parts by weight | of a polysiloxane stabilizer |
| 2.0 parts by weight | of diethanolamine |
| 0.1 parts by weight | of a 33% solution of diethylene triamine in dipropylene glycol and |

| -continued | |
|---|---|
| 0.1 parts by weight | of dimethylaminoethyl ether, | and the resulting mixture is foamed up in an open mold. A highly elastic flexible foam is obtained; its mechanical properties are summarized in Table 2.

EXAMPLE 16

44.0 parts by weight of the urea-modified polyisocyanate from Example 4 (NCO: 44.2%) are vigorously mixed with the previously prepared mixture described in Example 15 and foamed up in an open mold.

A highly elastic, flexible foam is obtained, which has the mechanical properties shown below in Table 2 in which they are compared with those of Example 15(biuret-modification).

TABLE 2

| | Example 15 | Example 16 |
|---|---|---|
| Gross density kg/m³ | 35 | 35 |
| Tensile strength KPa | 90 | 65 |
| Elongation at break % | 100 | 90 |
| Compression resistance KPa at 40% deformation | 2.5 | 2.4 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of aromatic polyisocyanates containing urea and/or biuret groups, optionally in the form of a mixture of homologues and/or isomers, which comprises reacting diisocyanates which are free from urea and biuret groups selected from the group consisting of aromatic diisocyanates with diamines having primary or secondary amino groups and which are free from urea and biuret groups at about 20° to 180° C., and at an equivalent ratio of isocyanate groups to amino groups in the range of about 5:1 to 100:1 without precipitating any insoluble urea and/or biuret constituents, wherein at least about 25 mol % of the diisocyanates put into the process correspond to the formula:

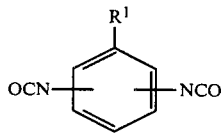

and/or at least about 25 mol % of the diamines put into the process correspond to the formula:

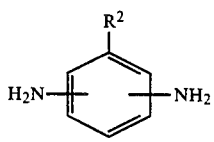

wherein
$R^1$ represents a saturated aliphatic hydrocarbon having 6 to 18 carbon atoms and.
$R^2$ represents a saturated aliphatic hydrocarbon having 10 to 13 carbon atoms.

2. The process of claim 1 which comprises removing at least a portion of the excess unmodified aromatic diisocyanates which are free from urea and biuret groups by thin layer distillation.

3. The process of claim 1 wherein about 100 mol % of the diamines put into the process correspond to the formula set forth in claim 1.

4. The process of claim 1 wherein said process is conducted in the absence of an auxiliary solvent other than the excess aromatic diisocyanate employed during the reaction.

* * * * *